US005733544A

United States Patent [19]

Marrone et al.

[11] Patent Number: 5,733,544

[45] Date of Patent: Mar. 31, 1998

[54] NEMATICIDAL BACILLUS STRAIN AND METABOLITE AND METHODS OF USE THEREOF

[75] Inventors: Pamela Gail Marrone; Denise C. Manker; Sherry D. Heins, all of Davis; Desmond R. Jiménez, Woodland, all of Calif.; James J. Germida, Saskatoon, Canada

[73] Assignees: University of Saskatchewan, Saskatoon, Canada; Agraquest, Inc., Davis, Calif.

[21] Appl. No.: 746,895

[22] Filed: Nov. 18, 1996

[51] Int. Cl.$^{6}$ .......................... A01N 63/00; A01N 63/02

[52] U.S. Cl. .......................... 424/93.46; 435/252.31; 435/832; 435/71.1; 435/71.2; 424/93.1; 424/282.1; 424/93.48; 424/93.461; 424/93.462; 424/234.1; 424/236.1; 424/246.1

[58] Field of Search .......................... 424/93.1, 93.48, 424/93.461, 93.462, 234.1, 236.1, 246.1; 435/71.1, 71.2

[56] References Cited

U.S. PATENT DOCUMENTS

| | | | |
|---|---|---|---|
| 4,190,495 | 2/1980 | Curtiss, III | 435/172.3 |
| 4,968,619 | 11/1990 | Curtiss, III | 435/252.33 |
| 4,999,192 | 3/1991 | Payne et al. | 424/93.451 |
| 5,093,120 | 3/1992 | Edwards et al. | 514/2 |
| 5,151,363 | 9/1992 | Payne | 435/252.5 |
| 5,208,017 | 5/1993 | Bradfisch et al. | 424/84 |
| 5,427,786 | 6/1995 | Payne et al. | 424/93.451 |

FOREIGN PATENT DOCUMENTS

94/21795 9/1994 WIPO .

OTHER PUBLICATIONS

Argauer et al., "Evidence for a novel insecticidally active exotoxin produced by the HD 116 strain of *Bacillus thuringiensis var. morrisoni*" *J. Entomol. Sci.* (1991) 26:205–213.

Lüthy, "Insecticidal toxins of *Bacillus thuriengiensis*" *FEMS Microbiol. Lett.* (1980) 8:1–7.

Forsberg et al. "*Bacillus thuringiensis: Its Effects in Environmental Quality*," National Research Council of Canada. (1976) 136 pages total.

Stonard et al., "Microbial secondary metabolites as a source of agrochemicals" *ACS Symposium Series* (1994) 551:25–36.

Birge, *Bacterial and Bacteriophage Genetics* 3rd ed., (1981), Springer–Verlag. A title page and table of contents are enclosed herewith.

Spear, "Biotechnology in Agricultural Chemistry" *ACS Symposium Series* (1987) 334:204–214.

Miller, "Single derivatization method for routine analysis of bacterial whole cell wallfatty acid methyl esters, including hydroxy acids," *J. Clin. Microbiol.* (1982) 16:584–586.

Bochner, B.R. (1989) "Sleuthing out bacterial identities," *Nature* 339:157–158.

*Primary Examiner*—Christopher S. F. Low
*Attorney, Agent, or Firm*—Morrison & Foerster LLP

[57] ABSTRACT

The present invention relates to a newly discovered *Bacillus sp.* strain which exhibits pesticidal activity. The supernatant of cultures of this novel isolate are also effective pesticidal agents. Also provided are methods of using the novel strain or supernatant for treatment or prevention of disease in plants or animals.

9 Claims, 4 Drawing Sheets

NEMATICIDAL BACILLUS STRAIN AND METABOLITE AND METHODS OF USE THEREOF

TECHNICAL FIELD OF THE INVENTION

This invention is in the field of biopesticides. More particularly, the present invention describes a novel, pesticidal strain of the bacterium *Bacillus sp.* which is active against nematodes. The bacterial strain of the present invention is also active against cockroach. This novel *Bacillus sp.* strain also produces a secondary metabolite in its supernatant which can be used as a biocontrol agent in the treatment and prevention of nematode infection in plants or animals and in the treatment of cockroach infestations.

BACKGROUND OF THE INVENTION

Every year 250 to 350 million dollars of chemical pesticides are used to control nematode infections on plants. Synthetic chemical pesticides are relatively expensive and, because of their toxicity to humans and wildlife, many have been banned from use. Many of the chemicals used for plant parasitic nematode control are toxic to humans, wildlife and other nontarget species. Also, some have leaked into the ground water. As a result, much research has been concentrated in the area of biopesticides which have the advantage of being cheaper to develop and safer for the environment.

One commonly-used biopesticide is the gram-positive bacterium *Bacillus thuringiensis*. Pesticidal *B. thuringiensis* strains are known to produce crystal proteins during sporulation which are specifically toxic to certain orders and species of insects and nematodes. (See, e.g., U.S. Pat. No. 4,999, 192 and U.S. Pat. No. 5,208,017). These proteinaceous endotoxins produced by *B. thuringiensis* also act as insecticidal agents against corn rootworm and other beetles. For instance, delta-endotoxin is synthesized by the *B. thuringiensis* sporulation cell and, upon ingestion by susceptible larvae, is transformed into a biologically-active moiety that destroys the gut epithelium of the insect. (See, e.g., U.S. Pat. No. 5,427,786 to Payne et al.). Although *B. thuringiensis* endotoxins have been shown to be effective pesticides as purified crystals, washed cell pellets and expressed proteins (e.g., U.S. Pat. Nos. 5,093,120 to Edwards et al. and 5,151, 363 to Payne), none of their supernatants have exhibited pesticidal activity with the exception of alpha, gamma-, sigma- and beta-exotoxins.

One *B. thuringiensis* thermostable metabolite, termed beta-exotoxin, has also been shown to have pesticidal properties. Burgjeron and Biache (1979), *Entomophaga* 11:279–284 report a beta-exotoxin that is active against the Colorado potato beetle (*Leptinotarsa decemlineata*). In addition, the known *B. thuringiensis* beta-exotoxin exhibits non-specific pesticidal activity; killing not only nematodes, but flies, armyworms and corn rootworms as well. Sigma exotoxin has a structure similar to beta-exotoxin and is active against Colorado potato beetle (Argauer et al. (1991) *J. Entomol. Sci.* 26:206–213). Alpha-exotoxin is toxic against larvae of Musca domestica Cluthy (1980) *FEMS Microbiol. Lett.* 8:1–7. Gamma-exotoxins are various proteolytic enzymes, chitinases, and proteases. The toxic effects of gamma-exotoxins are only expressed in combination with beta- or delta-exotoxin. Forsberg et al. (1976) "*Bacillus thuringiensis*: Its Effects in Environmental Quality," National Research Council of Canada. Stonard et al. (1994) *ACS Symposium Series* 551:25 report a water soluble secondary metabolite active against corn rootworm in the supernatant of a *Bacillus cereus* strain.

Thus, there remains a need for pesticidal *Bacillus sp.* strains which produce non-exotoxin, non-proteinaceous, active metabolites in their supernatant. There is also a need for a biocontrol agents which are specifically active against nematodes.

DISCLOSURE OF THE INVENTION

An isolated, pure culture of a novel *Bacillus chitinosporus* strain AQ746 and mutants and variants thereof exhibiting nematicidal activity are provided. Also provided is a nematicidal and insecticidal metabolite obtained from the supernatant of a culture of this novel strain. The present invention also provides methods of treating or protecting plants and animals from nematode infections using the novel strain or its metabolite. Methods of treating cockroach infestations are also provided.

MODES FOR CARRYING OUT THE INVENTION

Figure 1:
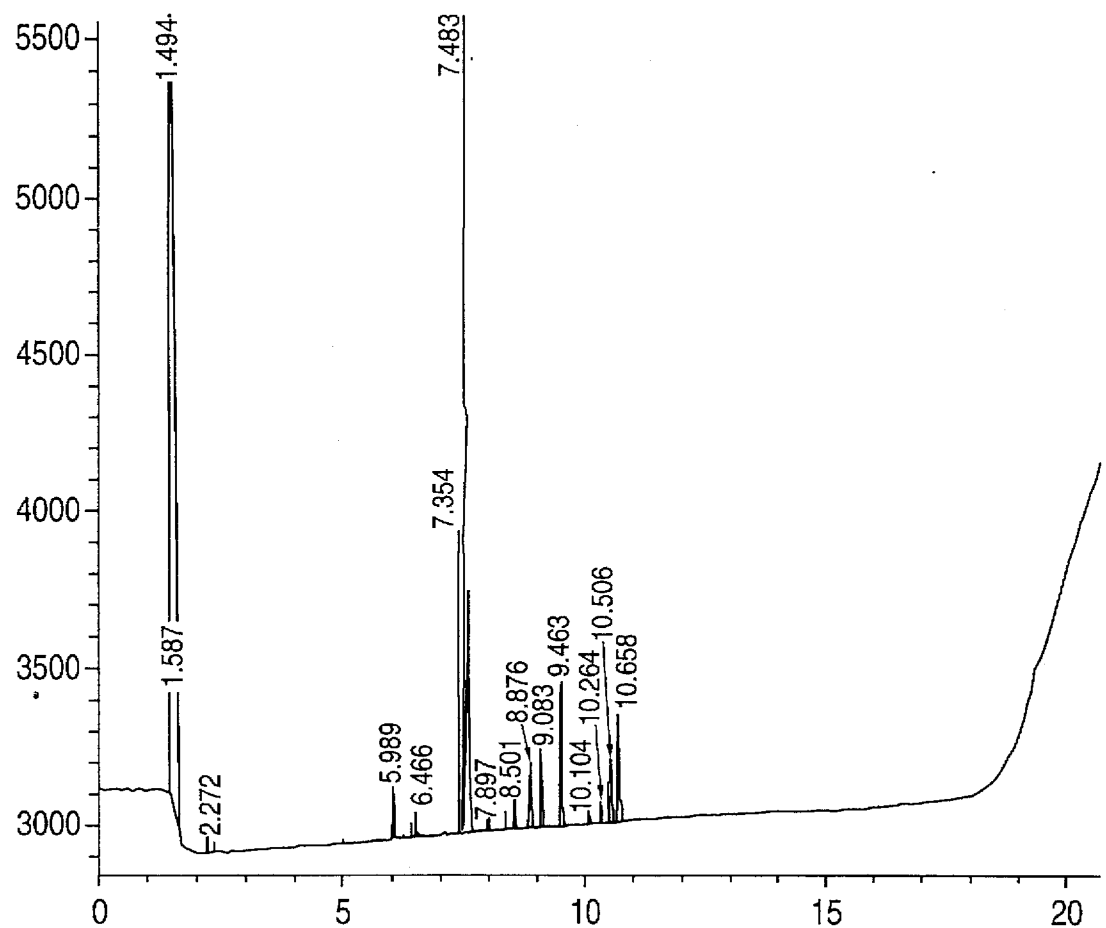
FIGS. 1, 2, 3 and 4 show four gas chromatography plots of strain AQ746 (NRRL Accession No. B-2161) whole-cell cellular fatty acids, derivatized to methyl esters (FAMEs) using the MIDI chromatography. Corresponding tabular results are found in Tables 1, 2, 3 and 4 respectively.

The present invention provides a novel isolate of a *Bacillus chitinosporus* strain which exhibits pesticidal activity. This strain is designated AQ746 and was isolated from plant roots and soil. This strain was deposited with the NRRL on Aug. 28, 1996 under the provisions of the Budapest Treaty on the International Recognition of the Deposit of Microorganisms for the Purposes of Patent Procedure under Accession No. B-21618. Another aspect of the invention is a metabolite that is effective in killing nematodes. The metabolite produced by the bacterial strain of the subject invention is unique because it is active against nematodes and cockroaches, but inactive against flies, corn rootworm, beet armyworm. This novel strain and its insecticidal and nematicidal metabolite have many advantages over chemical pesticides, particularly with respect to cost and environmental safety.

Definitions

As used herein, the term "insects" includes all organisms included in the class "Insecta." "Pre-adult" insects refers to any form of an organism prior to the adult stage, including, for example, eggs, larvae and nymphs. "Insecticidal" refers to the ability of a substance to increase mortality or inhibit the growth rate of insects. "Nematicidal" means the ability of a substance to increase mortality or inhibit the growth rate of nematodes. "Pesticidal" refers to the ability of a substance to increase mortality or inhibit the growth rate of insects, nematodes and/or flies. "Stunting" refers to a decreased rate of growth or abnormal development.

"Supernatant" refers to the liquid broth remaining when the cells grown in the broth are removed by centrifugation, filtration, sedimentation or any other means known in the art. The term "culturing" refers to the propagation of organisms on or in media of various kinds. The term "positive control" means a compound known to have pesticidal activity. "Positive controls" include, but are not limited to, commercially-available chemical pesticides. The term "negative control" means a compound known not to have pesticidal activity. Examples of negative controls include water or ethyl acetate.

As used herein, an "agent" includes natural or synthetic products, microorganisms, plant extracts and chemicals. A "test compound" is the agent being assayed for nematicidal or insecticidal properties. "Treatment" is an approach for obtaining beneficial or desired results. For the purposes of this invention, beneficial or desired results include, but are not limited to, alleviation of symptoms, diminishment of extent of infection, stabilized (i.e. not worsening) state of infection, prevent spread of infection, delay or slowing of infection progression, amelioration or palliation of the infection.

Thus, the present invention encompasses isolated, pure cultures of AQ746 which exhibit nematicidal and insecticidal activity. The *B. chitinosporus* strain of this invention may be grown in any conventional growth medium that supports *Bacillus sp*. Examples of suitable broth for culturing *Bacillus sp.*, include but are not limited to, a broth composed of peptone, dextrose, yeast extract and malt extract and a broth using the same ingredients as well as proflo cottonseed extract and soy flour. Solid substrates are also suitable for growing *Bacillus sp.*, strains. Growth procedures may also be readily scaled up to large fermentors by methods well known in the art.

Unlike known insecticidal *B. thuringiensis* isolates, the novel strain of this invention produces a nematicidal and insecticidal agent which is found in the supernatant when this strain is grown in culture. The supernatant may be obtained by any conventional means including centrifugation, filtration, sedimentation or the like.

The invention also encompasses methods of treating plants or animals infected with susceptible organisms with the novel Bacillus strain or its metabolite. The nematicidal and insecticidal metabolite of this invention may be formulated for use as a treatment by any method known in the art. For instance, the metabolite may be employed as a liquid or as a wettable powder, in granules or in dusts. Liquid formulations may be aqueous-based or non-aqueous-based and employed as foams, gels, suspensions, emulsifiable concentrates and the like. The formulations may be mixed with various materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants and the like.

Another aspect of the invention provides mutants or variants of the AQ746 strain which retain nematicidal and insecticidal activity and produce a nematicidal and insecticidal metabolite in their supernatant. Such mutants or variants have altered genotypic or phenotypic characteristics, and may be produced by genetic manipulation techniques well known in the art. (See, e.g., U.S. Pat. No. 4,190,495; U.S. Pat. No. 4,968,619; Edward A. Birge, BACTERIAL AND BACTERIOPHAGE GENETICS (1981); and Brian B. Spear, BIOTECHNOLOGY IN AGRICULTURAL CHEMISTRY, 204–214 (1987)). Examples of genetic mutants include, but are not limited to, mutants selected for phenotype by classical genetic methods and mutants created using recombinant techniques.

All patents and publications cited herein are incorporated by reference.

The following examples are provided to illustrate the invention. These examples are not to be construed as limiting.

EXAMPLES

Example 1

Culturing of novel Bacillus strain

A Bacillus strain isolated in 1993 from wheat roots in Saskatchewan, Canada and identified as TV8 was grown in two commonly used Bacillus culture media. Medium 1 contained peptone, dextrose, yeast extract and malt extract. Medium 2 contained the same ingredients and, in addition, proflo cottonseed extract and soy flour. One day old streaked cultures were used to inoculate either 250 mL baffled shake flasks or 15 mL culture tubes. Flasks or tubes were shaken at 200 rpm at 29° C. for 5 days. To assay pesticidal activity, 35 mL of culture broth were centrifuged at 5,200 rpm for 20 minutes and the supernatant used in microassay described in Example 2.

Identification and Characterization of the Bacillus strain

Figure 2:
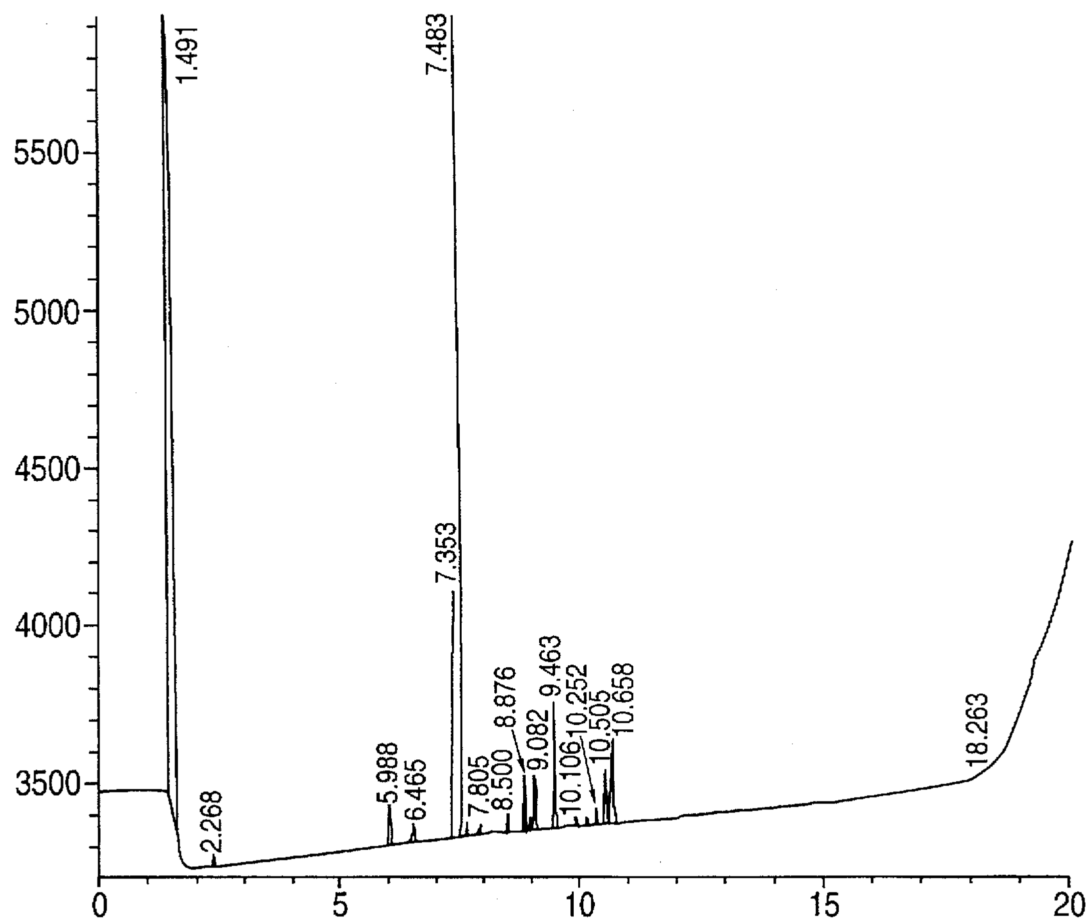
Figure 3:
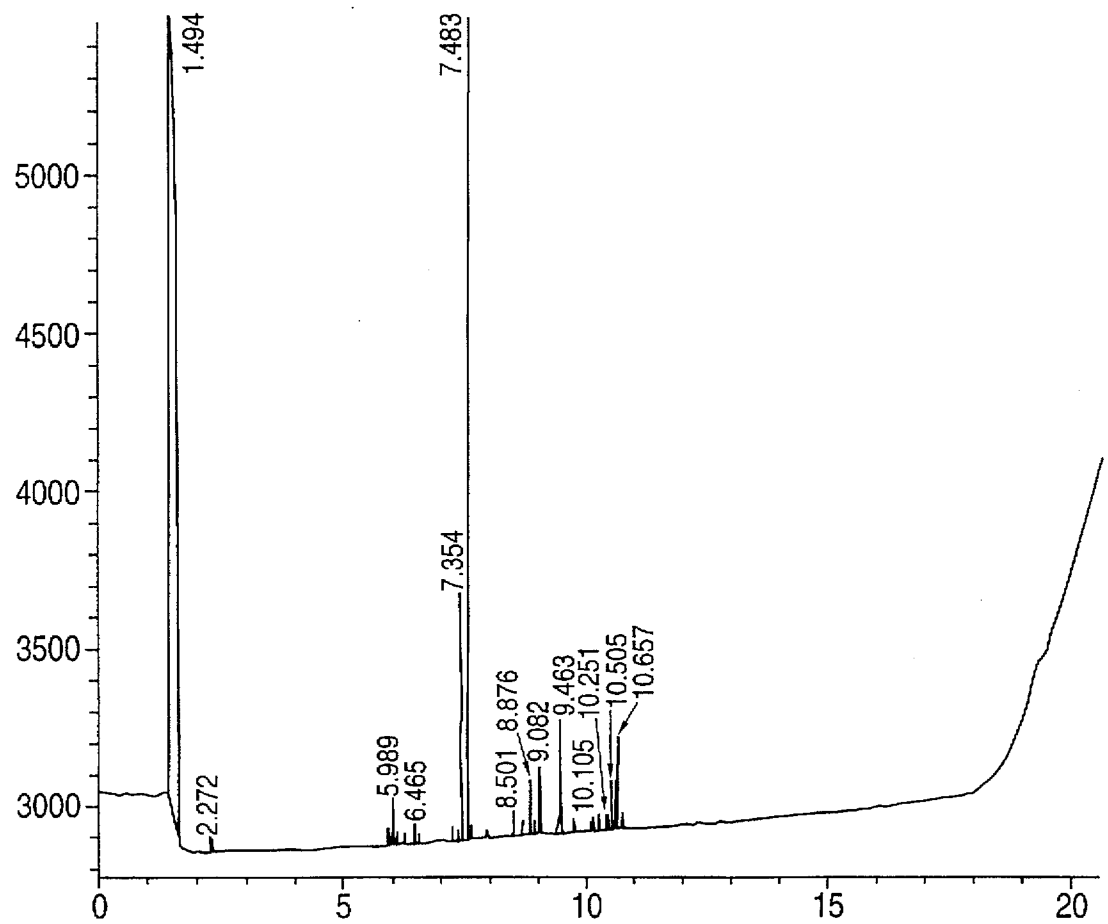
Figure 4:
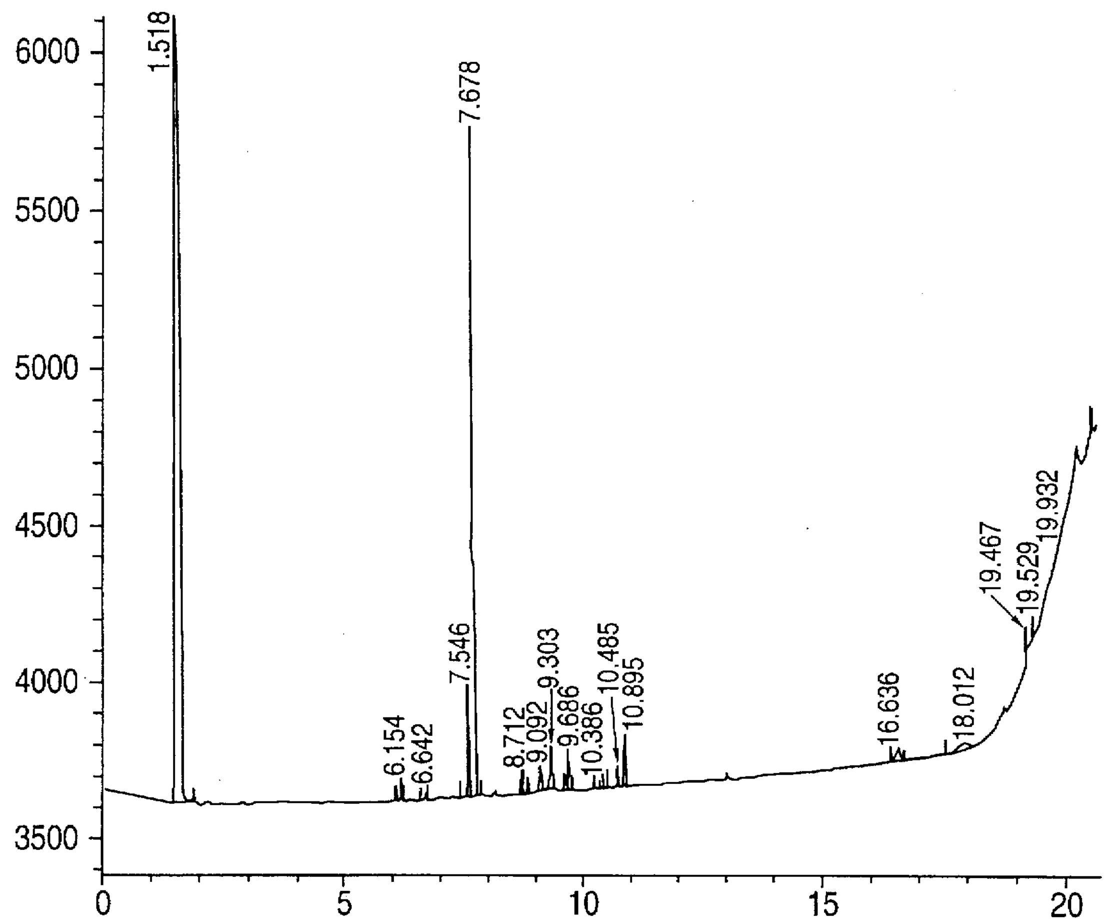

Using the Biolog microplate panel for identification (Biolog, Inc., Hayward, Calif.) and Microbial Identification System (MIDI) (Microbial Identification System, Inc., Newark, Del.), the strain was identified as *Bacillus chitinosporus* twice by MIDI (0.376 similarity index), but was also identified once as *B. megaterium* (0.298), *B. alvei* (0.364) and *B. brevis* (0.336). The MIDI profiles are shown in Tables 1 to 4 and in FIGS. 1 to 4.

Isolates were identified based on whole-cell fatty acids derivatized to methyl esters and analyzed by gas chromatography using MIDI. Isolates were grown on TSA (BBL) petri plates at 28° C. for 24 hours and the cells were then harvested. One mL of a methanolic NaOH (15% w/v) in 50% (v/v) methanol was added and the cells were saponified at 100° C. for 30 minutes. Esterification of fatty acids was performed with 2 mL of 3.25 N HCl in 46% (v/v) methanol at 80° C. for 10 minutes. The fatty acid methyl esters were extracted into 1.25 mL of 1:1 (v/v) methyl-tert-butyl ether-hexane and the organic extract washed with 3 mL of 1.2% (w/v) NaOH before analysis by gas chromatography. The gas chromatograph (Hewlett-Packard 5890A) was equipped with a flame ionization detector and capillary column (Hewlett-Packard no. 19091B-102, cross-linked 5% phenyl-methyl silicone; 25 m×0.22 mmID; film thickness, 0.33 μm; phase ratio, 150) with hydrogen as the carrier gas. Fatty acid methyl ester peaks were automatically integrated by a Hewlett-Packard 3392 integrator and bacterial isolates named using the MIDI Microbial Identification Software (Sherlock TSBA Library Version 3.80). The fatty acid methyl ester profile of *Xanthomonas maltophilia* ATCC 13637 was used as a reference check for the MIDI determination. See MIDI (1990) "Identification of bacteria by gas chromatography of cellular fatty acids," Technical Note #101. MIDI, Inc., 115 Barksdale Professional Center, Newark, Del.; Miller, L. T. (1982) "Single derivatization method for routine analysis of bacterial whole cell wall fatty acid methyl esters, including hydroxy acids," *J. Clin. Microbiol.* 16:584–586.

TABLE 1

Sherlock Version 1.06 DATA:C96905130A 05-SEP-96 13:38:44
ID:2607 WHEAT 3-TV8 (from slant) Date of run: 05-SEP-96 13:13:47
Bottle:23 SAMPLE (AEROBE)

| RT | Area | Ar/Rt | Respon | ECL | Name | % | Comment 1 | Comment 2 |
|---|---|---|---|---|---|---|---|---|
| 1.494 | 337699200 | 0.023 | — | 7.023 | SOLVENT PEAK | — | <min rt | |
| 1.587 | 3018 | 0.019 | — | 7.238 | — | — | <min rt | |
| 2.272 | 474 | 0.030 | — | 8.821 | — | — | <min rt | |
| 5.989 | 2022 | 0.031 | 1.005 | 13.618 | 14:0 ISO | 2.07 | *deviates –0.000 | Ref –0.001 |
| 6.466 | 1110 | 0.032 | 0.990 | 14.000 | 14:0 | 1.12 | *deviates –0.000 | Ref –0.001 |
| 7.354 | 12636 | 0.034 | 0.969 | 14.621 | 15:0 ISO | 12.50 | *deviates 0.000 | Ref –0.000 |
| 7.483 | 60318 | 0.035 | 0.966 | 14.711 | 15:0 ANTEISO | 59.48 | *deviates 0.000 | Ref –0.000 |
| 7.897 | 516 | 0.034 | 0.958 | 15.001 | 15:0 | 0.50 | *deviates 0.001 | Ref 0.001 |
| 8.501 | 1518 | 0.042 | 0.947 | 15.386 | 16:1 w7c alcohol | 1.47 | *deviates –0.000 | |
| 8.876 | 2946 | 0.036 | 0.941 | 15.625 | 16:0 ISO | 2.83 | *deviates –0.001 | Ref –0.002 |
| 9.083 | 3858 | 0.039 | 0.938 | 15.757 | 16:1 w11c | 3.69 | *deviates –0.000 | |
| 9.463 | 6840 | 0.038 | 0.933 | 15.999 | 16:0 | 6.51 | *deviates –0.001 | Ref –0.002 |
| 10.104 | 672 | 0.037 | 0.925 | 16.387 | ISO 17:1 w10c | 0.63 | *deviates –0.000 | |
| 10.254 | 1044 | 0.044 | 0.923 | 16.477 | Sum In Feature 5 | 0.98 | *deviates 0.001 | 17:1 ISO I/ANTEI B |
| 10.506 | 3228 | 0.041 | 0.920 | 16.630 | 17:0 ISO | 3.03 | *deviates 0.001 | Ref –0.001 |
| 10.658 | 5514 | 0.041 | 0.919 | 16.722 | 17:0 ANTEISO | 5.17 | *deviates –0.000 | Ref –0.002 |
| ****** | 1044 | — | — | — | Summed Feature 5 | 0.98 | 17:1 ISO I/ANTEI B | 17:1 ANTEISO B/i I |
| *ECL | | | | | | | | |

| Solvent Ar | Total Area | Named Area | % Named | Total Amnt | Nbr Rev | ECL Deviation | Ref ECL Shift |
|---|---|---|---|---|---|---|---|
| 337699200 | 10222 | 10222 | 100.00 | 97981 | 9 | 0.001 | 0.001 |

| Library | Rev | Match | Index |
|---|---|---|---|
| TSBA | [Rev 3.80)] | Bacillus | 0.298 |
| | | *B. megaterium* | 0.298 |
| | | B. m. GC subgroup B* | 0.298 |
| | | B. m. GC subgroup A* | 0.204 |
| | | *B. brevis** | 0.296 |
| | | *B. alvei** | 0.270 |
| CLIN | [Rev 3.80)] | Micrococcus | 0.189 |
| | | *M. leuteus* | 0.189 |
| | | M. 1. GC subgroup A | 0.189 |
| RHIZ-1 | [Rev 1.0] | *NO MATCH* | |

TABLE 2

Sherlock Version 1.06 DATA:C96822290A 22-AUG-96 09:28:17
ID:2340 WHEAT 3-TV8 (from slant) Date of run: 22-AUG-96 09:03:24
Bottle:6 SAMPLE (AEROBE)

| RT | Area | Ar/Rt | Respon | ECL | Name | % | Comment 1 | Comment 2 |
|---|---|---|---|---|---|---|---|---|
| 1.491 | 348839400 | 0.024 | — | 7.025 | SOLVENT PEAK | — | <min rt | |
| 2.268 | 468 | 0.025 | — | 8.826 | — | — | <min nt | |
| 5.988 | 1800 | 0.035 | 1.030 | 13.618 | 14:0 ISO | 2.39 | *deviates –0.000 | Ref 0.010 |
| 6.465 | 972 | 0.034 | 1.014 | 13.999 | 14:0 | 1.27 | *deviates –0.001 | Ref 0.009 |
| 7.353 | 10686 | 0.034 | 0.989 | 14.621 | 15:0 ISO | 13.63 | *deviates 0.000 | Ref 0.010 |
| 7.483 | 44604 | 0.035 | 0.985 | 14.712 | 15:0 ANTEISO | 56.69 | *deviates 0.001 | Ref 0.010 |
| 7.895 | 480 | 0.031 | 0.975 | 15.000 | 15:0 | 0.60 | *deviates –0.000 | Ref 0.009 |
| 8.500 | 888 | 0.037 | 0.961 | 15.386 | 16:1 w7c alcohol | 1.10 | *deviates –0.000 | |
| 8.876 | 2724 | 0.038 | 0.953 | 15.625 | 16:0 ISO | 3.35 | *deviates –0.001 | Ref 0.007 |
| 9.082 | 2688 | 0.038 | 0.948 | 15.757 | 16:1 w11c | 3.29 | *deviates –0.000 | |
| 9.463 | 6228 | 0.038 | 0.941 | 15.999 | 16:0 | 7.56 | *deviates –0.001 | Ref 0.007 |
| 10.106 | 498 | 0.037 | 0.929 | 16.388 | ISO 17:1 w10c | 0.60 | *deviates 0.001 | |
| 10.252 | 816 | 0.044 | 0.926 | 16.476 | Sum In Feature 5 | 0.97 | *deviates 0.000 | 17:1 ISO I/ANTEI B |
| 10.505 | 2886 | 0.040 | 0.922 | 16.630 | 17:0 ISO | 3.43 | *deviates 0.001 | Ref 0.006 |
| 10.658 | 4314 | 0.041 | 0.919 | 16.722 | 17:0 ANTEISO | 5.11 | *deviates 0.000 | Ref 0.006 |
| 18.263 | 168 | 0.067 | — | 21.210 | — | — | >max rt | |
| ****** | 816 | — | — | — | Summed Feature 5 | 0.97 | 17:1 ISO I/ANTEI B | 17:1 ANTEISO B/i I |
| *ECL | | | | | | | | |

| Solvent Ar | Total Area | Named Area | % Named | Total Amnt | Nbr Rev | ECL Deviation | Ref ECL Shift |
|---|---|---|---|---|---|---|---|
| 348839400 | 79584 | 79584 | 100.00 | 77519 | 9 | 0.001 | 0.008 |

| Library | Rev | Match | Index |
|---|---|---|---|
| TSBA | [Rev 3.80)] | Bacillus | 0.364 |
| | | *B. alvei** | 0.364 |
| | | *B. brevis** | 0.339 |
| | | *B. lentus* | 0.220 |
| CLIN | [Rev 3.80)] | Micrococcus | 0.215 |
| | | *M. leuteus* | 0.215 |
| | | M. 1. GC subgroup A | 0.215 |

TABLE 3

Sherlock Version 1.06 DATA:C96905130A 05-SEP-96 14:29:18
ID:2340 WHEAT 3-TV8 (from slant) Date of run: 05-SEP-96 14:04:30
Bottle:24 SAMPLE (AEROBE)

| RT | Area | Ar/Rt | Respon | ECL | Name | % | Comment 1 | Comment 2 |
|---|---|---|---|---|---|---|---|---|
| 1.494 | 336586200 | 0.023 | — | 7.025 | SOLVENT PEAK | — | <min rt | |
| 2.272 | 576 | 0.025 | — | 8.822 | — | — | <min rt | |
| 5.989 | 1824 | 0.032 | 1.002 | 13.618 | 14:0 ISO | 2.21 | *deviates 0.000 | Ref 0.000 |
| 6.465 | 1116 | 0.040 | 0.988 | 13.999 | 14:0 | 1.33 | *deviates –0.001 | Ref 0.000 |
| 7.354 | 10464 | 0.034 | 0.969 | 14.621 | 15:0 ISO | 12.23 | *deviates 0.000 | Ref 0.001 |
| 7.483 | 50760 | 0.035 | 0.966 | 14.712 | 15:0 ANTEISO | 59.17 | *deviates 0.001 | Ref 0.001 |
| 8.501 | 1344 | 0.040 | 0.949 | 15.386 | 16:1 w7c alcohol | 1.54 | *deviates 0.000 | |
| 8.876 | 2676 | 0.038 | 0.943 | 15.625 | 16:0 ISO | 3.05 | *deviates –0.001 | Ref –0.000 |
| 9.082 | 3336 | 0.039 | 0.940 | 15.757 | 16:1 w11c | 3.78 | *deviates –0.000 | |
| 9.463 | 5490 | 0.039 | 0.935 | 16.000 | 16:0 | 6.20 | *deviates –0.000 | Ref 0.000 |
| 10.105 | 1002 | 0.063 | 0.928 | 16.388 | ISO 17:1 w10c | 1.12 | *deviates 0.001 | |
| 10.251 | 1014 | 0.042 | 0.926 | 16.476 | Sum In Feature 5 | 1.13 | *deviates 0.000 | 17:1 ISO I/ANTEI B |
| 10.505 | 2538 | 0.042 | 0.924 | 16.630 | 17:0 ISO | 2.83 | *deviates 0.001 | Ref 0.000 |
| 10.657 | 4872 | 0.040 | 0.922 | 16.722 | 17:0 ANTEISO | 5.42 | *deviates –0.000 | Ref –0.001 |
| ****** | 1014 | — | — | — | Summed Feature 5 | 1.13 | 17:1 ISO I/ANTEI B | 17:1 ANTEISO B/i I |
| *ECL | | | | | | | | |

| Solvent Ar | Total Area | Named Area | % Named | Total Amnt | Nbr Rev | ECL Deviation | Ref ECL Shift |
|---|---|---|---|---|---|---|---|
| 336586200 | 86436 | 86436 | 100.00 | 82875 | 8 | 0.000 | 0.001 |

| | | | |
|---|---|---|---|
| TSBA | [Rev 3.80)] | Bacillus | 0.336 |
| | | *B. brevis** | 0.336 |
| | | *B. megaterium* | 0.290 |
| | | B. m. GC subgroup B* | 0.290 |
| | | B. m. GC subgroup A* | 0.214 |
| | | *B. alvei** | 0.259 |
| CLIN | [Rev 3.80)] | Micrococcus | 0.176 |
| | | *M. leuteus* | 0.176 |
| | | M. 1. GC subgroup A | 0.176 |
| RHIZ-1 | [Rev 1.0] | *NO MATCH* | |

TABLE 4

Sherlock Version 1.06 DATA:C94922552A 22-SEP-94 14:54:30
ID:2340 176 TV8 Date of run: 22-SEP-94 14:29:33
Bottle:24 SAMPLE (AEROBE)

| RT | Area | Ar/Rt | Respon | ECL | Name | % | Comment 1 | Comment 2 |
|---|---|---|---|---|---|---|---|---|
| 1.518 | 169261200 | 0.021 | — | 7.038 | SOLVENT PEAK | — | <min rt | |
| 6.154 | 1152 | 0.034 | 0.973 | 13.618 | 14:0 ISO | 2.40 | *deviates –0.000 | Ref 0.003 |
| 6.642 | 570 | 0.042 | 0.969 | 14.000 | 14:0 | 1.18 | *deviates –0.000 | Ref 0.003 |
| 7.546 | 4722 | 0.034 | 0.965 | 14.621 | 15:0 ISO | 9.74 | *deviates 0.000 | Ref 0.004 |
| 7.678 | 28926 | 0.035 | 0.964 | 14.712 | 15:0 ANTEISO | 59.62 | *deviates 0.001 | Ref 0.004 |
| 8.712 | 1230 | 0.037 | 0.963 | 15.387 | 16:1 w7c alcohol | 2.53 | *deviates 0.001 | |
| 9.092 | 1530 | 0.041 | 0.963 | 15.625 | l6:0 ISO | 3.15 | *deviates –0.001 | Ref 0.002 |
| 9.303 | 2574 | 0.045 | 0.963 | 15.758 | 16:1 w11c | 5.30 | *deviates 0.001 | |
| 9.686 | 2034 | 0.037 | 0.963 | 15.999 | 16:0 | 4.19 | *deviates –0.001 | Ref 0.001 |
| 10.336 | 618 | 0.046 | 0.964 | 16.388 | ISO 17:1 w10c | 1.27 | *deviates 0.001 | |
| 10.485 | 1164 | 0.045 | 0.964 | 16.477 | Sum In Feature 5 | 2.40 | *deviates 0.001 | I7:1 ISO I/ANTEI B |
| 10.741 | 1278 | 0.041 | 0.964 | 16.630 | 17:0 ISO | 2.63 | *deviates 0.001 | Ref 0.002 |
| 10.895 | 2712 | 0.041 | 0.964 | 16.722 | I7:0 ANTEISO | 5.59 | *deviates –0.000 | Ref 0.001 |
| 16.636 | 2238 | 0.110 | — | 20.087 | — | — | >max rt | |
| 18.012 | 1488 | 0.129 | — | 20.896 | — | — | >max rt | |
| 19.467 | 540 | 0.033 | — | 21.751 | — | — | >max rt | |
| 19.529 | 408 | 0.047 | — | 21.787 | — | — | >max rt | |
| 19.932 | 1404 | 0.092 | — | 22.024 | — | — | >max rt | |
| ****** | 1164 | — | — | — | Summed Feature 5 | 2:40 | 17:1 ISO I/ANTEI B | 17:1 ANTEISO B/i I |
| *ECL | | | | | | | | |

| Solvent Ar | Total Area | Named Area | % Named | Total Amnt | Nbr Rev | ECL Deviation | Ref ECL Shift |
|---|---|---|---|---|---|---|---|
| 169261200 | 48510 | 48510 | 100.00 | 46780 | 8 | 0.001 | 0.003 |

| | | | | |
|---|---|---|---|---|
| TSBA | [Rev 3.80)] | Bacillus | 0.376 | (not an approved name) |
| | | *B. chitinosporus* | 0.376 | (not an approved name) |
| | | *B. brevis** | 0.315 | |
| | | *B. megaterium* | 0.247 | |

TABLE 4-continued

| | | | |
|---|---|---|---|
| | | B. m. GC subgroup B** | 0.247 |
| | | B. m. GC subgroup A* | 0.200 |
| CLIN | [Rev 3.80] | *NO MATCH* | |

Comparison with TSBA [Rev 3.80]: *Bacillus-chitinosporus (not an approved name)* Distance: 4.523

| | 0 | 5 | 10 | 15 | 20 | 25 | 30 | 35 | 40 | 45 | 50 | 55 | 60 | 65 | 70 | 75 | 80 | 85 | 90 | 95 | 100 |
|---|---|---|---|---|---|---|---|---|---|---|---|---|---|---|---|---|---|---|---|---|---|
| . | | | | | | | | | | | | | | | | | | | | | |
| 13:0 ANTIESO | x+ | . | . | . | . | . | . | . | . | . | . | . | . | . | . | . | . | . | . | . | |
| 14:0 ISO | . | x+ | . | . | . | . | . | . | . | . | . | . | . | . | . | . | . | . | . | . | |
| 14:0 | x | + | . | . | . | . | . | . | . | . | . | . | . | . | . | . | . | . | . | . | |
| 15:0 ISO | . | . | . | +x | . | . | . | . | . | . | . | . | . | . | . | . | . | . | . | . | |
| 15:0 ANTIESO | . | . | . | . | . | . | . | . | . | . | . | . | +x | . | . | . | . | . | . | . | |
| | | | | | | | | | | | | | – | | | | | | | | |
| 15:0 | x+ | | | | | | | | | | | | | | | | | | | | |
| 16:1 w/c alcohol | +x | . | . | . | . | . | . | . | . | . | . | . | . | . | . | . | . | . | . | . | |
| 16:0 ISO | . | +x | . | . | . | . | . | . | . | . | . | . | . | . | . | . | . | . | . | . | |
| 16:00 w11c | . | x+ | . | . | . | . | . | . | . | . | . | . | . | . | . | . | . | . | . | . | |
| 16:0 | . | *– | . | . | . | . | . | . | . | . | . | . | . | . | . | . | . | . | . | . | |
| ISO 17:1 w10C | . | x+ | . | . | . | . | . | . | . | . | . | . | . | . | . | . | . | . | . | . | |
| 17:0 ISO | . | +x | . | . | . | . | . | . | . | . | . | . | . | . | . | . | . | . | . | . | |
| 17:0 ANTIESO | . | +x | . | . | . | . | . | . | . | . | . | . | . | . | . | . | . | . | . | . | |
| SUMMED FEATURE 5 | +x | . | . | . | . | . | . | . | . | . | . | . | . | . | . | . | . | . | . | . | |

In addition to being characterized by MIDI, isolates were assessed for carbon substrate utilization using the Biolog microplate panel (Biolog, Inc., Hayward, Calif.). The Biolog microplate is comprised of prefilled and dried panel wells with 95 different carbon substrates. Isolates were grown in liquid medium at 28° C. for 24 hours and then the cell suspensions were washed in 0.85% saline. The washed cell suspension was used to inoculate each panel well of a Gram Position Microplate (Biolog, Inc., Hayward, Calif.). After incubating the Microplate at 28° C. for 24 hours, carbon utilization reactions were assessed. Substrate utilization profiles were then compared to the Biolog Gram-Positive Data Base (release 3.50) and matched to the closest specie. See, Bochner, B. R. (1991) "Identification of over 500 Gram-negative species by a single test panel," *Amer. Clin. Lab.* April, p. 14; Bochner, B. R. (1989) "Sleuthing out bacterial identities," *Nature* 339:157–158. AQ746 gave a score of 0.445 in the Biolog test (*Bacillus pasteurii*).

Example 2

Assaying pesticidal activity of bacillus strain

Assays were performed in 96-well microplates. Each well contained a solid agar substrate, a test organism suspension and either a positive control, a negative control or supernatant obtained as described in Example 1 from the *Bacillus sp.* strain.

Test organisms used were either pre-adult corn rootworms (e.g., *Diabrotica virgifera*, *D. longicornis* or *D. undecimpunctata*), pre-adult beet armyworms (*Spodoptera exigua*), pre-adult flies (*Drosophila melanogaster*), the N2 strain of the nematode *Caenorhabditis elegans* or pre-adult German cockroach (*Blatella germanica*). Test organisms were diluted in 0.1% agar to a concentration of approximately 5 organisms/25 uL.

To assay nematicidal activity, an agar substrate was prepared for the wells of the microplate by pouring 975 mLs of deionized water into a 1 liter bottle. Three grams of sodium chloride (NaCl), 2.5 grams of peptone, 17.0 grams of bactoagar and 1.0 mL of a 5 mg/mL solution of cholesterol in ethanol were added to the bottle. The contents were sterilized at a minimum of 15 psi, 250° F. for 30 minutes. After sterilization, 1.0 mL of a filter-sterilized 1M $CaCl_2$ solution, 1.0 mL of a filter sterilized 1M $MgSO_4$ solution, and 25.0 mL of a filter sterilized, 1M, pH 6.0 solution of $KH_2HPO_4$ were added. 200 uL was dispensed into each well of a 96-well microplate, and the plates allowed to cool. For testing the other insects, the same procedure was used, except a wheat-germ-based medium was dispensed into the 96-well microplate. The formulation for the wheat-germ-based medium is prepared as follows. 1 L of wheat germ diet is prepared with 14.5 g agar, 13.8 g alphacel (celufil), 38.5 g sucrose, 32.25 g casein, 27.48 g wheat germ, 9.25 g Wesson salt mix, 1.0 g methyl paraben, 1.0 g sorbic acid, 0.4 mL linseed oil, 0.064 g streptomycin, 0.064 g chlorotetracycline, 9.0 g Vanderzants vitamin mix, 3.0 mL of propionic acid/phosphoric acid solution (418 mL propionic acid and 42 mL of phosphoric acid and 540 mL water), and 5.0 mL of 190 proof EtOH and 840 mL of water. The components are dissolved and then sterilized.

A 1 ppm solution of Avid® was used as a positive control. Deionized water was used as a negative control. Two replicates of test sample or control were used for each assay. 40 uL of supernatant sample prepared as described in Example 1 was dispensed onto the agar surface of microplate wells. A 25 uL aliquot of the pre-adult organism suspension was dispensed into each sample well. The plates were then placed in a fume hood to dry for approximately 2 to 3 hours until the agar solution was dried, but the eggs were not overdried. The microplate was sealed with an airtight substance such as Mylar®, and each well ventilated with a pin press. The plates were incubated at 27° C. for up to 7 days.

After incubation, wells were scored by noting neonate mortality or the degree of larval development. Sample wells containing all dead or stunted larvae were given a score of 1, wells containing some dead and other severely stunted larvae were given a score of 2, live but stunted larvae were scored as 3 and sample wells containing no dead larvae were given a score of 4. Scores were averaged among replicates within each sample. Results are summarized in Table 5.

TABLE 5

| | Pesticidal Activity of AQ746 Superatant Score Rating | | | | |
|---|---|---|---|---|---|
| Test No. | C. elegans | Corn rootworm | Beet armyworm | Fly | German cockroach |
| 1 | 2.0 | 4.0 | 4.0 | 4.0 | 1.0 |
| 2 | 2.0 | 4.0 | 4.0 | 4.0 | 4.0 |
| 3 | 4.0 | 4.0 | 4.0 | 4.0 | 4.0 |
| 4 | 2.0 | 4.0 | 4.0 | 4.0 | 1.0 |

These results show that the novel *B. chitinosporus* strain produces a metabolite in its supernatant which is effective against nematodes and cockroaches, but not against corn rootworm, armyworm or flies.

Having now fully described this invention, it will be appreciated by those skilled in the art that the same can be performed within a wide range of equivalent parameter, concentrations and conditions without departing from the spirit and scope of the invention and without undue experimentation. While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows the scope of the appended claims.

What is claimed is:

1. An isolated, pure culture of a novel strain of *Bacillus chitinosporus*, designated AQ746, NRRL Accession Number B-21618 or mutants thereof which maintain all of the identical characteristics of the deposited strain, which strain secretes a toxic metabolite having nematicidal and insecticidal activity.

2. The culture of claim 1 wherein the novel strain of *Bacillus chitinosporus* which secretes the toxic metabolite having nematicidal and insecticidal activity does not have pesticidal activity against corn rootworm.

3. An isolated soluble toxic metabolite obtained from the centrifuged supernatant of a culture of *Bacillus chitinosporus*, designated AQ746, NRRL Accession Number B-21618 or mutants thereof which maintain all of the identical characteristics of the deposited strain, such that said toxic metabolite has nematicidal and insecticidal activity.

4. A method of treating a nematode infection in a plant or an animal comprising administering an effective amount of the culture of claim 1 for a time and under conditions effective to control the nematode infection.

5. A method of treating a nematode infection in a plant or an animal comprising administering an effective amount of the culture of claim 2 for a time and under conditions effective to control the nematode infection.

6. A method of treating a nematode infection in a plant or an animal comprising administering an effective amount of the metabolite of claim 3 for a time and under conditions effective to control the nematode infection.

7. A method of treating cockroach infestation comprising administering an effective amount of the culture of claim 1 for a time and under conditions effective to control cockroach infestation.

8. A method of treating cockroach infestation comprising administering an effective amount of the culture of claim 2 for a time and under conditions effective to control cockroach infestation.

9. A method of treating cockroach infestation comprising administering an effective amount of the metabolite of claim 3 for a time and under conditions effective to control cockroach infestation.

* * * * *